United States Patent [19]

von der Heyde et al.

[11] Patent Number: 5,556,563

[45] Date of Patent: Sep. 17, 1996

[54] TICK REMOVAL DEVICE COMPRISING ELECTRICALLY HEATED RETRACTABLE TWEEZERS

[76] Inventors: Christian P. von der Heyde, 81 McNeil Cir., Marlborough, Mass. 01752; Michael E. Backus, 256 Webster St., Newton, Mass. 02166

[21] Appl. No.: 419,729

[22] Filed: Apr. 10, 1995

[51] Int. Cl.⁶ .................... A61B 17/50; H05B 1/00
[52] U.S. Cl. ................ 219/227; 606/210; 606/28; 294/99.2; 294/100; 43/134
[58] Field of Search .................. 219/229, 227, 219/228, 230, 231, 233, 243; 606/210, 211, 51, 52, 205, 206, 28–31, 45; 294/99.2, 93, 94, 100, 119.1, 166, 168; 43/134, 135; 83/15, 16, 170, 171

[56] References Cited

U.S. PATENT DOCUMENTS

| | | | |
|---|---|---|---|
| 3,420,563 | 1/1969 | Witt | 294/99.2 |
| 3,844,291 | 10/1974 | Moen | 606/210 |
| 3,938,527 | 2/1976 | Rioux et al. | 606/51 |
| 4,213,460 | 7/1980 | Weiner | 606/131 |
| 4,240,435 | 12/1980 | Yazawa et al. | 606/210 |
| 4,303,268 | 12/1981 | Davidson | 294/99.2 |
| 4,393,872 | 7/1983 | Reznik et al. | 606/206 |
| 4,442,837 | 4/1984 | Keatley | 606/210 |
| 4,979,771 | 12/1990 | Childs, III | 606/51 |
| 5,002,323 | 3/1991 | Idsund | 294/100 |
| 5,035,695 | 7/1991 | Weber, Jr. et al. | 606/45 |
| 5,250,046 | 10/1993 | Lee | 606/211 |
| 5,276,306 | 1/1994 | Huffman | 219/229 |
| 5,376,087 | 12/1994 | Haber et al. | 606/29 |
| 5,407,243 | 4/1995 | Riemann | 606/210 |

FOREIGN PATENT DOCUMENTS

| | | | |
|---|---|---|---|
| 3002088 | 7/1981 | Germany | 294/99.2 |
| 3624250 | 2/1988 | Germany . | |
| 628792 | 3/1982 | Switzerland | 294/100 |

*Primary Examiner*—John A. Jeffery
*Attorney, Agent, or Firm*—William Nitkin

[57] ABSTRACT

A device for removing a tick attached to an animal or person having a tweezer with first and second tweezer arms disposed within a casing, such tweezer arms movable within first and second channels defined on the inside of the casing with the front tips of the tweezer arms extendible and retractable through an opening in the front of the casing, the channels tapering inwardly to direct the tips of the tweezer arms together as they pass through the opening. A power source is provided which can be a battery disposed within the casing and interconnected to the first and second tweezer arms. An electrical circuit is completed when the tweezer arms are in their forward advanced position extending out the opening of the casing to heat the tweezer arms and the tick grasped therebetween.

3 Claims, 2 Drawing Sheets

5,556,563

TICK REMOVAL DEVICE COMPRISING ELECTRICALLY HEATED RETRACTABLE TWEEZERS

BACKGROUND OF THE INVENTION

1. Field of the Invention

The device of this invention resides in the area of devices for removing ticks from animals and people and more particularly relates to an extendible and retractable tweezer disposed in a casing which tweezer, upon extension, automatically grips the tick and heats up to cause the tick to release its grip.

2. Description of the Prior Art

There are many hand tools which use heated tweezer-like elements for removing a tick from the skin of an animal. For example, U.S. Pat. No. 4,213,460 to Weiner discloses forceps with an electrical current passing therethrough to provide heat with the forceps having oppositely aligned cup-shaped members to surround and remove the tick. U.S. Pat. No. 4,979,771 to Childs, III also discloses the use of cup members at the end of tweezer-like elements to surround the tick. U.S. Pat. No. 5,276,306 to Huffman teaches the use of a heated needle which, when poked into the tick, causes the tick to release its grip, and the tick can then be scooped off the skin by a spoon member disposed below the needle.

SUMMARY OF THE INVENTION

It is an object of this invention to provide a convenient and effective device to remove a tick attached to the skin of an animal or person, such device incorporating a heated tweezer which device utilizes an internal battery as a source of power for such heat or which can be plugged into normal house current by a cord. In the tick removal device of this invention the tweezer is disposed within a casing such that the tweezer arms slide within inwardly tapered channels formed on the interior of the casing and are disposed so that as they pass through an opening in the front of the casing, the tweezer arms are forced together by the shape of the channels to lock onto the tick. As the tweezer arms come together and close on the tick, an electrical circuit is completed within the casing which allows electrical current to flow to, and heat, the two tweezer arms which, in turn, heat the tick to cause it to release its grip on the animal or person.

It is a further object of this invention to provide a heated tick removal device, the heated tweezer arms of which are substantially shielded both from the user's hands and from the animal from which the tick is to be removed.

DESCRIPTION OF THE PREFERRED EMBODIMENT(S)

Figure 1:
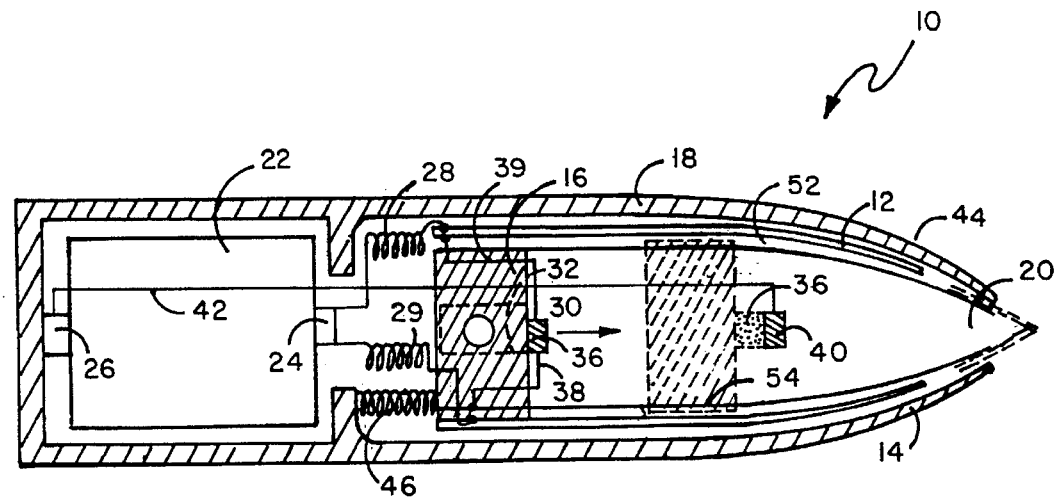
FIG. 1 illustrates a top cross-sectional view through the tick removal device of this invention.
Figure 2:
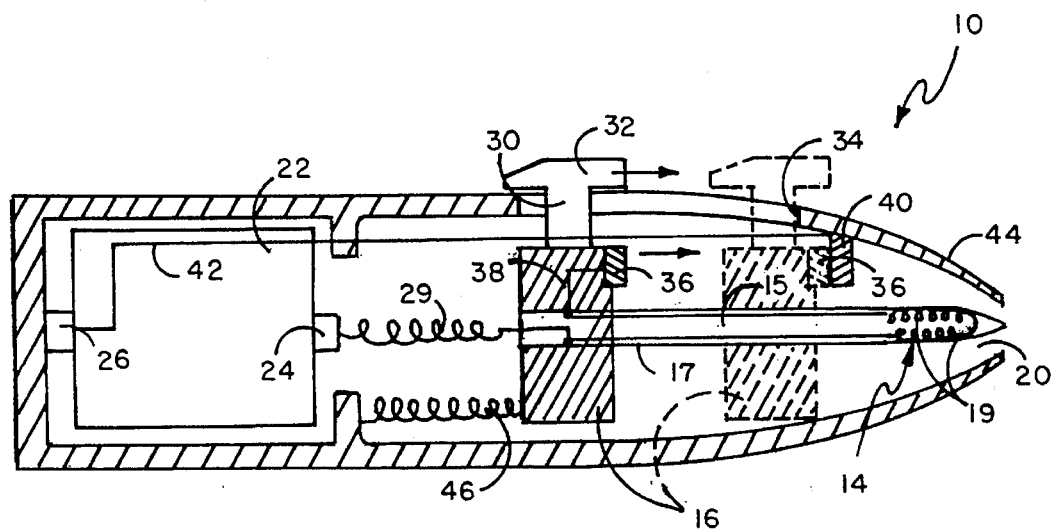
FIG. 2 illustrates a side cross-sectional view through the device of this invention.
Figure 3:
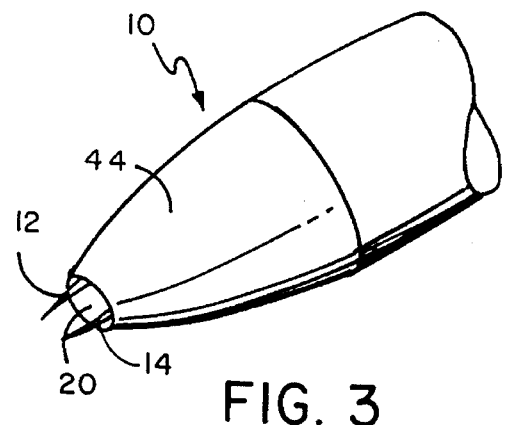
FIG. 3 illustrates a front perspective view of the opening at the front of the device of this invention with the pointed tips of the tweezer arms starting to emerge.
Figure 4:
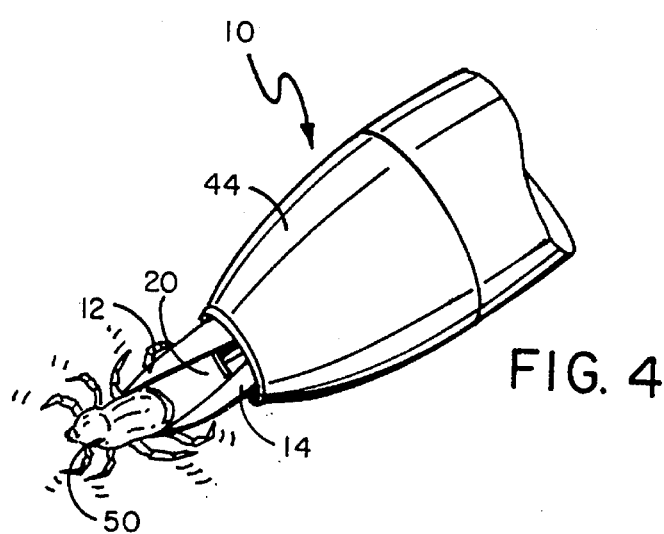
FIG. 4 illustrates the view of FIG. 3 with the tweezer arms fully emerged and gripping a tick.
Figure 5:
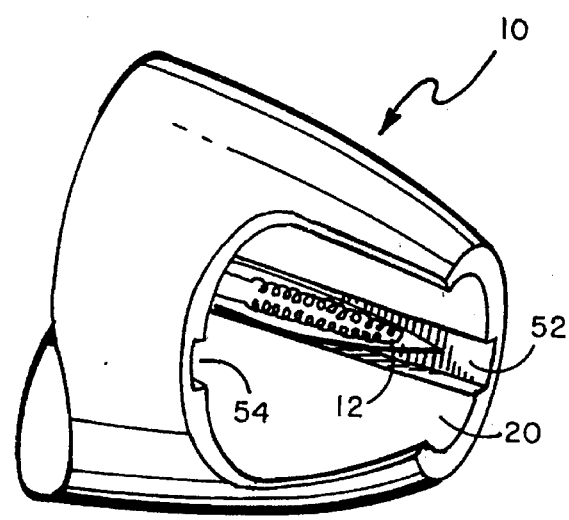
FIG. 5 illustrates a perspective cutaway view of the device of this invention.

FIG. 1 illustrates a top cross-sectional view of the tick removal device 10 of this invention showing a pair of metal, thin and flexible tweezer arms being first tweezer arm 12 and second tweezer arm 14 which are disposed within casing 18. Casing 18 has a hollow interior, the front of which tapers to opening 20. The shape of the device in a preferred embodiment can be elongated and bullet-shaped for ease of handling although other shapes can be utilized. The first ends of the tweezer arms can be pointed to grasp the tick and are aimed toward opening 20 at front portion 44 of the casing. The rearwardly disposed second ends of the tweezer arms are attached to slide member 16 which is slideably fitted within casing 18. Shaft 30 is attached to slide member 16 and extends upwards through longitudinal slot 34 formed in the top of the casing as better seen in FIG. 2. Push knob 32 is disposed on top of shaft 30 and is manually movable forward and backward. Forward movement of push knob 32 is indicated in FIG. 2 by the direction of the arrow from the solid line depiction to the dotted line depiction. First and second tweezer arms 12 and 14 of the tweezer ride, respectively, within inwardly tapered first and second channels 52 and 54, as seen in FIG. 5, formed on opposite sides of the interior wall of casing 18 such that they are always aligned with one another. First and second channels 52 and 54 taper inwardly toward opening 20. As push knob 32 is advanced, it moves attached shaft 30 within slot 34 which, in turn, advances slide member 16 which moves attached second ends of the tweezer arms forward, causing the front first ends of the tweezer arms to emerge from opening 20 and start to come together. The inwardly tapering first and second channels 52 and 54 positioned opposite to one another force the pointed first ends of the tweezer arms to precisely come together to grip tick 50 as seen in FIG. 4.

Heat can be provided to the tweezer arms as described below. As seen in FIG. 2 electrical contact is made to first pole 24 of a power source, such as battery 22 which is located in the rear portion of the casing, by electrical wires 28 and 29 which are, respectively, attached to first and second tweezer arms 12 and 14. Power from a house current wall plug, for example, can also be used through a step-down transformer not shown but well known as a power source. Electrical wire 42 extends from second pole 26 of the battery to an activation contact 40 which is disposed on the inside of the casing near the front of slot 34 which activation contact 40 makes contact with a second contact 36 attached by electrical wires 38 and 39 to second tweezer arm 14 and first tweezer arm 12, respectively, such that when the tweezer is in an advanced position with push knob 32 moved forward, second contact 36 moves against activation contact 40 which completes the circuit through battery 22, causing the heating of the tweezer arms, each of which contains an upper wire 15 and lower wire 17, as seen for example in tweezer arm 14 in FIG. 2, connected near their tips by a ni-chrom coil 19 which heats when the circuit is completed as, for example, through electrical wire 29 connected to lower wire 17, and electrical wire 38 connected to upper wire 15.

As seen in FIG. 5, first and second channels 52 and 54 can be formed within the interior walls of casing 18, and they taper inwardly toward one another on opposite sides of the interior wall of casing 18 to cause the tweezer arms to be perfectly aligned opposite to one another as they move forward through opening 20 to come toward one another to grasp the tick such that the heat in each tweezer arm causes the tick to release its grip. As seen in FIGS. 1 and 2, spring 46 can pull slide member 16 rearwards when push knob 32 is released to quickly retract the tips of the tweezer arms back into the casing.

Although the present invention has been described with reference to particular embodiments, it will be apparent to those skilled in the art that variations and modifications can be substituted therefor without departing from the principles and spirit of the invention.

We claim:

1. A device for the removal of a tick attached to an animal or person, comprising:

a casing having a front end, a rear end and an interior cavity defined therein, said casing having an exterior wall, an interior wall and an opening defined in said casing at said front end;

first and second channels defined in said interior wall disposed opposite to one another and tapering inwardly toward one another at the front of said casing;

first and second tweezer arms, each having a pointed first end and a second end, said first and second tweezer arms disposed, respectively, within said first and second channels;

a slide member having a top, said slide member interconnected to said second ends of said tweezer arms;

control means to move said slide member within said casing, said slide member in its use mode adapted to be moved from a first rearward position to a second forward position to advance said first and second tweezer arms within said first and second channels out said opening in said front end of said casing and move said pointed ends toward one another by said tweezer arms' contact with said inwardly tapering channels, said tweezer arms moving closer together as they extend out said front end of said casing to grasp said tick, and in its storage mode to be moved rearward from its second forward position to its first rearward position, allowing said tweezer arms to spread apart; and means to heat said first and second tweezer arms when said first and second tweezer arms are in their second forward position to heat a tick when grasped by said first ends of said first and second tweezer arms to cause said tick to release its grip on said animal or person.

2. The device of claim 1 wherein said control means comprises:

a longitudinal slot defined in said casing;

a shaft member having a top, said shaft member attached to said top of said slide member and extending up through said slot;

a knob member disposed on said top of said shaft member for manual movement forward and rearward of said slide member and attached tweezer arms; and a spring member disposed within said casing to return said slide member to its first rearward position when said knob member is released from its second forward position.

3. The device of claim 2 wherein said means to provide electrical current to heat said tweezer arms comprises:

a battery located within said casing; and means to provide current from said battery to said first tweezer arms when said first and second tweezer arms are, respectively, in their second forward position.

* * * * *